United States Patent [19]

Braeunling et al.

[11] Patent Number: 5,182,348

[45] Date of Patent: Jan. 26, 1993

[54] ARYLMETHYLOLS, THEIR PREPARATION AND THEIR USE

[75] Inventors: Hermann Braeunling, Burghausen; Richard Becker, Emmerting; Georg Bloechl, Traunreut, all of Fed. Rep. of Germany

[73] Assignee: Wacker-Chemie GmbH, Munich, Fed. Rep. of Germany

[21] Appl. No.: 746,932

[22] Filed: Aug. 19, 1991

[30] Foreign Application Priority Data

Aug. 29, 1990 [DE] Fed. Rep. of Germany ....... 4027253

[51] Int. Cl.$^5$ .................. C08F 28/06; C08F 26/06; C07D 207/30; C07D 409/06; C07D 233/52; C07D 233/28

[52] U.S. Cl. .................. 526/256; 526/256; 526/258; 526/259; 526/268; 526/270; 252/950; 548/454; 548/455; 548/468; 548/470; 548/517; 548/518; 548/525; 548/527; 548/531; 548/532; 548/557; 548/558; 548/560; 549/49; 549/58; 549/59; 549/60; 549/61; 549/68; 549/71; 549/74; 549/75; 549/76; 549/79; 549/81

[58] Field of Search ............... 252/950; 526/256, 258, 526/259, 268, 270; 548/454, 455, 468, 470, 517, 518, 525, 527, 531, 532, 557, 558, 560; 549/49, 58, 59, 60, 61, 68, 71, 74, 75, 76, 79, 81

[56] References Cited

PUBLICATIONS

CA 83(21):177759u Kinetic . . . type. Walper et al. p. 468, 1975.
CA 111(21):193976q Reactions . . . radicals. Savchenko et al. p. 700, 1989.
CA 115(14):136898z Polyarylmethines; . . . properties. Braeunling et al. p. 136, 1991.
CA 115(16):171687b Polydiheteroarylenemethines—. . . polymers. Braeunling et al., 1991.
CA 81(3):12618t Study of . . . with ESR, Koorstra et al. p. 264, 1974.
Synthetic Metals, 41-43 (1991) 1539-1547 (Braunling et al. Polyarylmethines . . . Polymers.
Synthetic Metals, 41-43 (1991) 487-491, Braunling et al., Polydiheteroarylene methines . . . Polymers.

*Primary Examiner*—Mary C. Lee
*Assistant Examiner*—Joseph K. McKane
*Attorney, Agent, or Firm*—Collard & Roe

[57] ABSTRACT

Compounds of the formula (1)

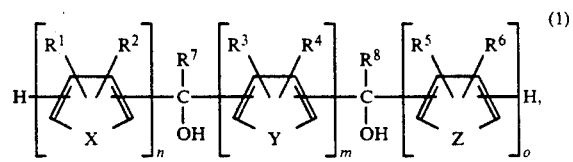

wherein $R^1$, $R^2$, $R^3$, $R^4$, $R^5$, $R^6$, $R^7$ and $R^8$ have the meanings given in the description, and the other radicals have the following meanings:

X, Y and Z denote identical or different divalent radicals —O—, —S—, —N($R^9$)— or —C($R^{10}$)=C($R^{11}$)—, with the proviso that at least one of the radicals, X, Y and Z is not a radical of the formula —C($R^{10}$)=C($R^{11}$)—, and wherein $R^9$ is a hydrogen atom, a branched or unbranched $C_1$- to $C_8$-alkyl radical or an optionally substituted phenyl radical, and $R^{10}$ and $R^{11}$ are, in each case, identical or different radicals which have one of the meanings of $R^1$, $R^7$ and $R^8$ denote identical or different radicals, that is to say hydrogen atoms or $C_1$- to $C_6$-alkyl or phenyl radicals, and n, m and o denote identical or different integers with a value of from 1 to 10.

Also provided are a process for the preparation of these compounds, processes for their polymerization, novel polymers which can be prepared in this manner and the use of the polymers.

8 Claims, 2 Drawing Sheets

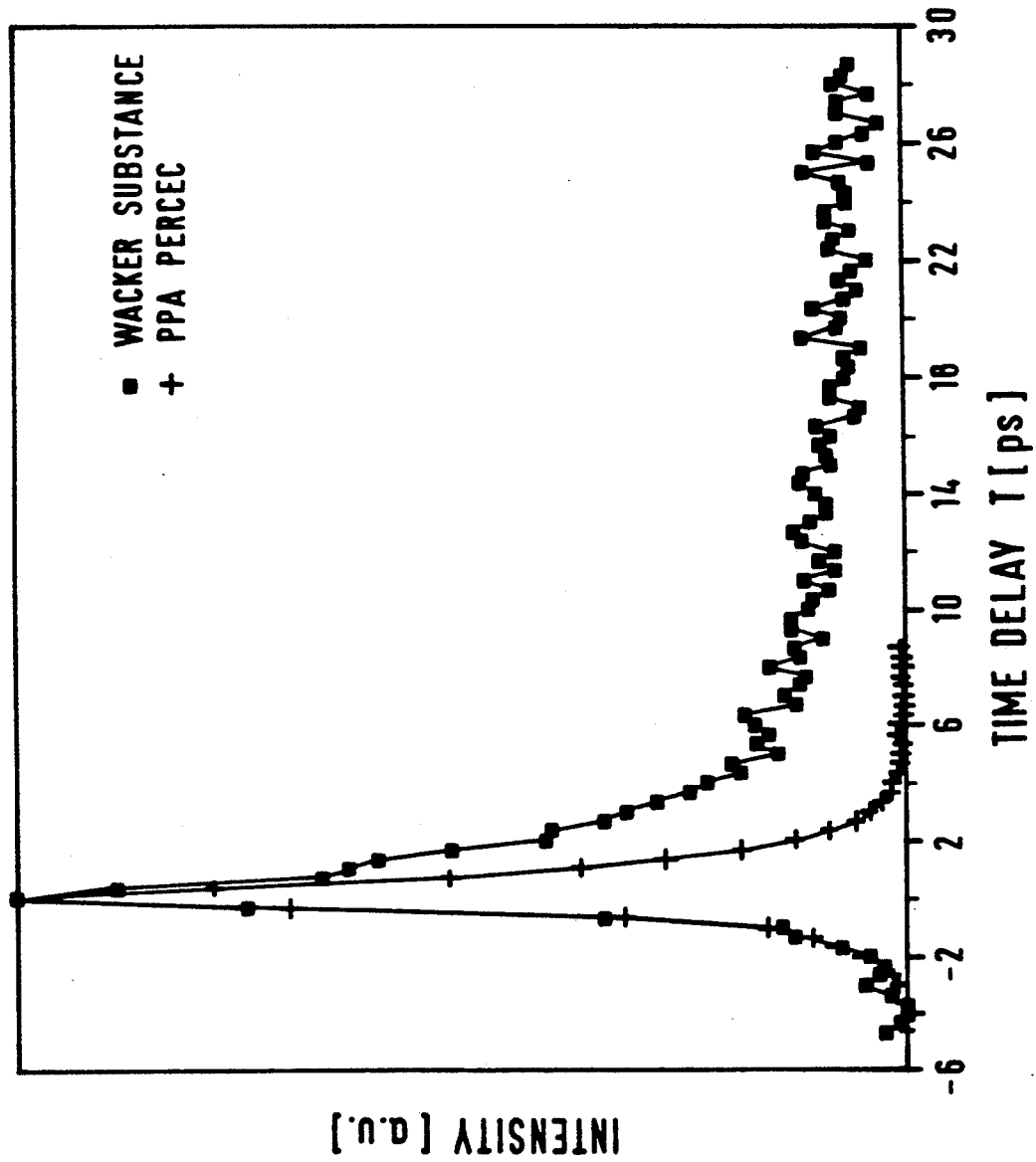

ARYLMETHYLOLS, THEIR PREPARATION AND THEIR USE

BACKGROUND OF THE INVENTION

1. Field of the Invention

The present invention relates to a certain novel bis-[di(hetero)arylhydroxymethyl](hetero)aromatics and processes for their preparation and their polycondensation, in particular, to give conductive polymers.

2. The Prior Art

W. Broser et al [Tetrahedron, vol. 31, pp. 1769–1779 (1975)] describe bis-[diarylhydroxymethyl]aromatics of the formula A—CH(OH)—B—CH(OH)—A. In these, the radicals A denote biphenylyl or terphenylyl radicals, and the radicals B denote phenylene, optionally alkylated biphenylene radicals, terphenylene, napthylene and phenylene-alkylene-phenylene radicals.

Conductive polypyrroles and copolymers thereof are described, inter alia, in European Patent Application No. 99,984. Polymers with conjugated double bonds in which (hetero)aromatic nuclei are, in each case, bonded to one another by a carbon atom are described in European Patent Application No. 218,093. Polymers which consist of the same heteroaromatics which are linked to one another alternately directly, or via a methine group, can be prepared, inter alia, according to World Publication No. 87/00678.

SUMMARY OF THE INVENTION

It is an object of the present invention to provide for the synthesis of novel substances, in particular, novel intermediate products for the preparation of polymers having electrically conductive or non-linear optical properties.

It is a further object of the present invention to provide a novel process for the preparation of polymers.

It is an additional object of the present invention to prepare novel polymers.

It is yet another object of the present invention to prepare thin layers of the polymers on substrates which are suitable for use for optical, electrooptical and electronic purposes.

The present invention has the following advantages: With the aid of the polymers according to the invention, or their starting substances, it is also possible to prepare polymer coatings having a thickness of less than 1 μm, which was hitherto difficult or impossible because of the volatility of the starting substances and/or their tendency to crystallize.

Furthermore, the polymers according to the invention can also be prepared with less reactive condensing agents than, for example $POCl_3$. This is advantageous, since such strong condensing agents often give rise to undesirable side reactions.

Novel Arylmethylols

The above objects are accomplished, in accordance with the present invention, by compounds of the formula (1)

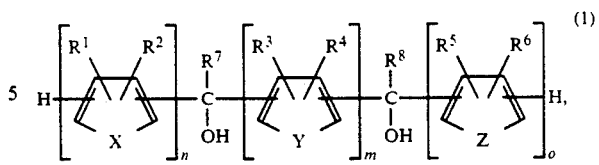

wherein $R^1$, $R^2$, $R^3$, $R^4$, $R^5$ and $R^6$ denote identical or different radicals on the rings, for example, hydrogen atoms, halogen atoms, straight-chain or branched $C_1$- to $C_6$-alkyl radicals, $C_1$- to $C_6$-alkylcarboxylic acid radicals or esters thereof with $C_1$- to $C_4$-alkanols, $C_1$- to $C_6$-alkylamino radicals or nitro or cyano groups, wherein at least two of the radicals $R^1$, $R^2$, $R^3$, $R^4$, $R^5$ and $R^6$ can be linked to one another in pairs and form a trimethylene or tetramethylene group or form a polynuclear (hetero)aromatic with the ring to which they are bonded;

X, Y and Z denote identical or different divalent radicals —O—, —S—, —N($R^9$)— or —C($R^{10}$)=C($R^{11}$)—, with the proviso that at least one of the radicals X, Y and Z is not a radical of the formula —C($R^{10}$)=C($R^{11}$)— and wherein $R^9$ is a hydrogen atom, a branched or unbranched $C_7$- to $C_8$-alkyl radical or an optionally substituted phenyl radical;

$R^{10}$ and $R^{11}$ are, in each case, identical or different radicals which have one of the meanings of $R^1$;

$R^7$ and $R^8$ denote identical or different radicals, that is to say, hydrogen atoms or $C_1$- to $C_6$-alkyl or phenyl radicals; and n, m and o denote identical or different integers with a value of from 1 to 10, and the reaction of these compounds in the presence of dehydrating agents to give polymers.

Preferred compounds of the formula (1) are those of the formula (2)

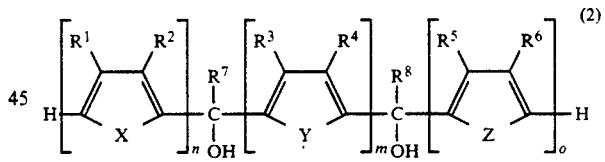

wherein $R^1$, $R^2$, $R^3$, $R^4$, $R^5$, $R^6$, $R^7$, $R^8$, X, Y, Z, m, n and o have the meanings given under formula (1).

n, m and o in the above-mentioned formulae and in the formula shown below preferably assume values from 1 to 4, in particular, in each case, identical or different values of 1 or 2. The values for n and o are preferably the same. The radicals X, Y and Z in the above-mentioned formulae and in the formulae shown below are preferably radicals of the formula —O—, —S—, —NH— or —N($CH_3$)—. The radicals X and Z in the above-mentioned formulae and in the formulae below are preferably identical. The radicals $R^7$ and $R^8$ in the above-mentioned formulae and in the formulae shown below are preferably, in each case, hydrogen atoms.

The radicals $R^1$, $R^2$, $R^3$, $R^4$, $R^5$ and $R^6$ in the above-mentioned formulae and the formulae below are preferably hydrogen atoms or $C_1$- to $C_4$-alkyl radicals, or at least two of the radicals $R^1$, $R^2$, $R^3$, $R^4$, $R^5$ and $R^6$ are linked to one another in pairs, so that they form a polynuclear (hetero)aromatic with the ring to which they are bonded. The radicals $R^1$, $R^2$, $R^3$, $R^4$, $R^5$ and $R^6$ are, in particular, hydrogen atoms or $C_1$- to $C_4$-alkyl radicals. At least one of the radicals $R^1$ and $R^2$, at least one of the radicals $R^3$ and $R^4$ and/or at least one of the radicals $R^5$ and $R^6$ are preferably a hydrogen atom. Preferred compounds of the formula (1) or (2) are those of the formula (8):

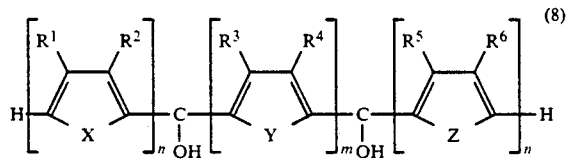

wherein $R^1$, $R^2$, $R^3$, $R^4$, X, Y, m and n have the meanings given under formula (1).

Particularly preferred compounds of the formula (1), (2) or (8) are compounds of the formula (3):

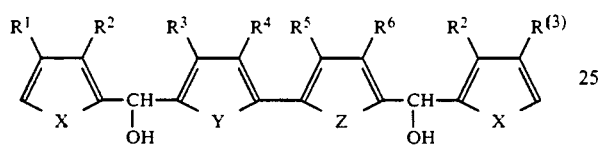

wherein X, Y, Z, $R^1$, $R^2$, $R^3$, $R^4$, $R^5$ and $R^6$ have the above-mentioned meanings.

Process for the Preparation of the Arylmethylols

The novel arylmethylols of the formula (1), (2), (3) or (8) according to the invention can be prepared by reaction of compounds of the formula (4) with compounds of the formulae (5) and (6)

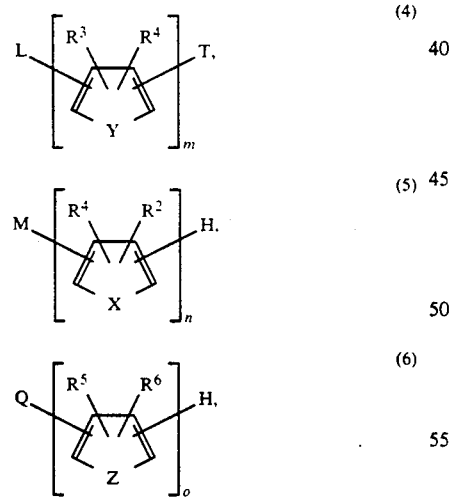

wherein either
 the two radicals L and T are radicals from the group comprising hydrogen atoms, metal atoms and radicals of the formula —MgI, —MgBr and —MgCl and
 M is a radical of the formula —C($R^7$)=O and
 Q is a radical of the formula —C($R^8$)=O,
or
 the two radicals M and Q are radicals from the group comprising hydrogen atoms, metal atoms and radicals of the formula —MgI, —MgBr and —MgCl and L is a radical of the formula —C($R^7$)=O, and
 T is a radical of the formula —C($R^8$)=O, and
 wherein $R^1$, $R^2$, $R^3$, $R^4$, $R^5$, $R^6$, $R^7$, $R^8$, X, Y, Z, m, n and o have the meanings given under formula (1).

One compound of the formula (4) or also a mixture of at least two compounds of the formula (4) can be employed in the process according to the invention. One compound of the formula (5) and/or one compound of the formula (6), or also mixtures of at least two compounds of the formula (5) and/or at least two compounds of the formula (6) can be employed. All the other reaction participants, catalysts, solvents, inert gases, doping agents, coating substances, further polymers, plasticizers and auxiliaries of all types employed in this process or in processes described below can also, in each case, be employed individually or as a mixture of at least two substances of this type.

The radicals of the above-mentioned formulae (5) and (6) are preferably chosen so that the compound of the formula (5) is identical to that of the formula (6).

The process according to the invention is, thus, preferably carried out by reaction of a compound of the formula (9) with a compound of the formula (10):

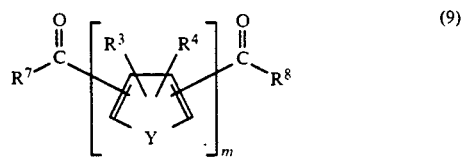

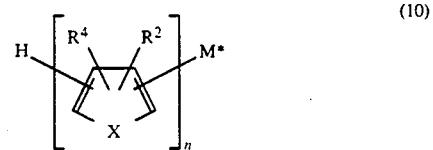

or by reaction of a compound of the formula (11) with a compound of the formula (12):

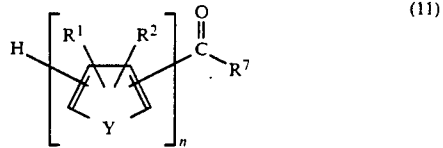

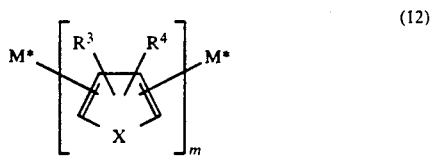

wherein, the above-mentioned formulae (9), (10), (11) and (12), the radicals $R^1$, $R^2$, $R^3$, $R^4$, $R^7$, $R^8$, X, Y, m and n have the meanings given under the formula (1); and M* in each case, denotes identical or different radicals which are selected from the group comprising hydrogen atoms, metal atoms, preferably alkali metal atoms, in particular lithium, and radicals of the formula —MgCl, —MgBr and —MgI. The radicals M* are preferably, in each case, identical radicals. If the radicals M* are, in each case, hydrogen atoms, the reaction is preferably carried out in the presence of acids or bases. Preferably, however, the radicals M* are metal atoms, in particular, alkali metal atoms, or radicals of the formula —MgBr, —MgCl or —Mg—I. The lithium atom is the particularly preferred radical M*.

The starting substances are preferably employed in the process according to the invention in amounts such that the ratio of the sum of the numbers of moles of the compounds of the formulae (5) and (6) to the number of moles of the compounds of the formula (4) is 20:1 to 0.1:1, in particular, 1.5:1 to 2.5:1. In certain cases, a large excess of a component which is inexpensive or easy to remove may be appropriate, so that the reaction essentially proceeds to completion.

The process according to the invention is preferably carried out at temperatures of from $-80°$ C. to $+200°$ C., particularly preferably from $-40°$ C. to $+100°$ C., in particular, from $-20°$ C. to $+30°$ C.

The reaction can, in each case, be carried out under the pressure of the surrounding atmosphere, that is to say, under about 0.1 MPa (absolute). It is also possible for higher pressures, for example, up to 2 MPa (absolute) to be applied. Lower pressures, for example, down to a minimum of 1 Pa (absolute) are used, in particular, if substances, such as starting substances, by-products, auxiliaries, solvents and the like, are to be distilled off from the reaction mixture during the reaction.

The process according to the invention can be carried out in the presence or in the absence of solvents. If solvents are used, which is preferred, solvents or solvent mixtures having a boiling point or boiling range of up to 120° C. under 0.1 MPa are preferred. Examples of such solvents are water; alcohols such as methanol, ethanol, n-propanol and iso-propanol; ethers such as dioxane, tetrahydrofuran, diethyl ether and diethylene glycol dimethyl ether; chlorinated hydrocarbons, such as methylene chloride, chloroform, carbon tetrachloride, 1,2-dichloroethane and trichloroethylene; hydrocarbons, such as pentane, n-hexane, hexane isomer mixtures, heptane, octane, wash benzine, petroleum ether, benzene, toluene and xylenes; ketones such as acetone, methyl ethyl ketone and methyl isobutyl ketone; carbon disulfide and nitrobenzene, or mixtures of these solvents.

The designation solvent does not mean that all the reaction components must dissolve in this. The reaction can also be carried out in a suspension or emulsion of one or more reaction partners. The reaction can also be carried out in a solvent mixture with a miscibility gap, in each case, at least one reaction partner being soluble in each of the mixed phases.

If at least one of the radicals L, T, M, Q and M* in the above-mentioned formulae (4), (5), (6), (10) and (12) does not denote a hydrogen atom, which is preferred, the process is carried out in the absence of protic solvents. Preferred solvents in this case are, in particular, diethyl ether, tetrahydrofuran, 1,4-dioxane, benzene and toluene It may be appropriate to carry out the reaction in the absence of considerable amounts of water and/or in the presence of an inert gas. This is particularly advisable if at least one of the reactants contains a metal atom or a radical of the formula —MgBr or —MgCl. In this case, the inert gas should also be essentially free from $CO_2$. Examples of such inert gases are nitrogen, argon and mixtures thereof.

The reactants of the formulae (4), (5), (6), (9), (10), (11) and (12) are commercially available in some cases, and in some cases they can be prepared by known processes. Thus, most of the heteroarylaldehydes of the formula (11) where n=1 are commercially available.

Biheteroaryldialdehydes of the formula (9) (m=2) can be prepared, for example, by reaction of the corresponding halogenoheteroarylaldehydes with copper powder (Ullmann reaction). The lithium or Grignard compounds of the formulae (10) and (12) are prepared by reaction of the corresponding halogen compounds of the heteroaromatics and biheteroaromatics with n-butyllithium or magnesium metal in a manner which is known per se or by reaction of the heteroaromatics and biheteroaromatics with n-butyllithium.

Preparation of Polymers

Polymers containing (hetero)arylenemethine units can be prepared from the above-mentioned compounds of the formulae (1), (2), (8) and (3) by polycondensation. The polycondensation is preferably carried out in the presence of a condensing agent, for example, from the group comprising acid chlorides, acid anhydrides and strong acids, bases and hygroscopic compounds. Examples of hygroscopic compounds are $CaCl_2$, KOH, $CuSO_4$, $Co(NO_3)_2$ and other similar compounds, in each case, in the dried form without water of crystallization. Examples of such acid chlorides are $SOCl_2$, $POCl_3$, $PCl_5$ and p-toluenesulfonyl chloride; examples of such acid anhydrides are acetic anhydride, trifluoromethanesulfonic anhydride, $P_4O_{10}$, $SO_3$ and trifluoroacetic anhydride. Examples of such strong acids are p-toluenesulfonic acid, sulfuric acid, $C_1$- to $C_8$-alkyl- or arylsulfonic acids, fluorosulfonic acid and chlorosulfonic acid. Examples of bases are Lewis bases, such as the hydroxyl ion, the methanolate and the ethanolate ion and the isopropanolate ion, halide ions, such as fluoride, chloride, bromide and iodide ions, the cyanide ion, the hydride ion, carbon monoxide, ammonia, amines, ethers, such as diethyl ether, tetrahydrofuran and 1,3-dioxane, and water; Bronsted bases, such as alkali metal and alkaline earth metal hydroxides, such as LiOH, NaOH, KOH, RbOH, CsOH, $Mg(OH)_2$, $Ca(OH)_2$, $Sr(OH)_2$ and $Ba(OH)_2$, and amides, such as sodium and potassium amide, and hydrides, such as sodium, potassium and calcium hydride.

If the condensing agent is insoluble or only slightly soluble in the reaction mixture, it may be advantageous to add a suitable solubilizing substance, a substance which accelerates phase transfer and/or a substance which disperses the condensing agent or to employ the condensing agent in a corresponding formulation.

The condensing agent can be removed after the condensation together with the condensate which has been split off, in particular, if possible, by distillation.

If condensing agents are used in the process according to the invention, those which are gaseous at a temperature of 80° C. under a pressure of 0.1 MPa are preferred. It is particularly preferable to employ condensing agents in the amounts of 0.5 mol to 2 mol, in particular 1 mol to 2 mol, per mol of the compounds of the formula (1) employed. If the condensation is to be accelerated by condensing agents, a high rate of reaction is also achieved with catalytic amounts of condensing agents if the water formed in the course of the reaction is removed from the reaction mixture by suitable physical methods, for example, by azeotropic distillation.

The polycondensation according to the invention can be carried out in the presence of solvents. As regards the choice and examples of such solvents, that which has been mentioned above in connection with solvents which can be used in the process for the preparation of the arylmethylols applies accordingly. However, in many cases, the use of protic solvents is not a disadvantage.

Preferred solvents are acetone, methanol, ethanol, tetrahydrofuran, methylene chloride and chloroform.

Black pulverulent polymers which are built up from units of the formula (13):

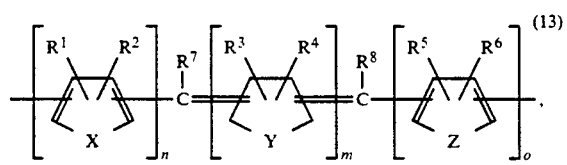

wherein $R^1$, $R^2$, $R^3$, $R^4$, $R^5$, $R^6$, $R^7$, $R^8$, X, Y, Z, m, n and o have the meanings given under formula (1) and the broken circular segment in the middle aryl ring of the formula represents a conjugated double bond, are obtained as the product of the polycondensation according to the invention.

Polymers prepared according to the invention, in which at least one of the radicals $R^1$, $R^2$, $R^3$, $R^4$, $R^5$ and $R^6$ is an alkyl radical, are often soluble in organic solvents, such as $CH_2Cl_2$ and tetrahydrofuran. The other polymers according to the invention are, in general, not noticeably soluble in the usual organic solvents.

Thin polymer layers, inter alia layers which are thinner than one micrometer, can be prepared by the polycondensation according to the invention of compounds of the formula (1) to give polymers build up from units of the formula (13). The nature and strength of the condensing agent, if such an agent is required at all, depends on the structure and reactivity of the compounds of the formula (1) employed. The compounds of the formula (1), in general, require condensing agents, if at all, which are less strong and, therefore, less reactive and can be condensed in layers of less than one $\mu$m. Trifluoroacetic acid vapor is an example of such a less reactive condensing agent which has been employed successfully in the polycondensation according to the invention. Layers can be prepared, inter alia, by dissolving a certain amount of a condensing agent together with one or more compounds of the formula (1), if appropriate with cooling, applying the solution to a substrate and distilling off the solvent or allowing it to evaporate.

The polymers thus obtainable are electrically conductive or semiconductive compounds.

The conductivity of the polymers can be increased further by addition of known doping substances.

Examples of doping agents are alkali metals, such as sodium or potassium; proton acids, such as $H_2SO_4$, $HClO_4$, $H_2Cr_2O_7$, HI and $HNO_3$; and Lewis acids, such as $SbCl_5$, $AsCl_5$, $TiCl_4$, $FeCl_3$, $SnCl_4$, $ZnCl_2$, $AsF_5$ and halogen, such as, for example, iodine. The treatment of the compositions according to the invention with doping agents (n) is, in general, carried out such that the vapors or solutions of the doping agent are allowed to act on the polymers. The process is usually carried out at about 10° C. to 30° C., usually with exclusion of moisture, and often with exclusion of air. The doped polymers preferably contain 0 to 50, particularly preferably 0.01 to 30, in particular, 0.1 to 20 percent by weight of doping agent.

Doping agents can be added before, during or after the polycondensation. If condensing agent is employed for the polycondensation according to the invention, doping agent can be added before, during or after the addition of condensing agent.

If surfaces of silicon, glass or quartz are coated with solutions or melts of the compounds of the formula (1) by processes which are known per se, and the coated carriers are exposed to gaseous or vaporous condensing agents, if appropriate, after evaporation of the solvent, thick, usually blue-colored coatings are initially formed, which discolor to dark brown to black after some time. Some of these coatings have a metallic surface gloss. The coatings with pure compounds of the formula (1), in most cases, have the disadvantage that the films have a poor adhesion and shrink and tear during the condensation process. However, if the compounds of the formula (1) are dissolved together with another polymer; in other words, a polymer which cannot be prepared by polycondensation of compounds of the formula (1), preferably one or more thermoplastic polymers, firmly adhering and stable films are obtained. All soluble polymers or polymers which can be swollen by solvents or the reactants can, in principle, be employed as the polymers.

Compositions can be obtained in this manner by a procedure in which the polymer which can be prepared by the process according to the invention is present, in finely divided form, in the other polymer or in the other polymers.

Examples of such suitable other polymers are organic synthetic polymers, in particular, thermoplastic polymers, such as polyvinyl chloride, polyethylene, polypropylene, polyvinyl acetate, polycarbonate, polyacrylate, polymethacrylate, polymethyl methacrylate, polystyrene, polyacrylonitrile, polyvinylidene chloride, polyvinyl fluoride, polyvinylidene fluoride, polyvinylidene cyanide, polybutadiene, polyisoprene, polyether, polyester, polyamide, polyimide, silicones, polyvinyl alcohol, polyvinylpyrrolidone, polyacrylamide, polyethylene glycol and derivatives thereof and similar polymers, including copolymers, such as styrene-acrylate copolymers, vinyl acetate-acrylate copolymers and ethylene vinyl acetate copolymers, as well as naturally occurring polymers, such as cellulose, starch, casein and natural rubber, and also semisynthetic high molecular weight compounds, such as cellulose derivatives, for example, methylcellulose, hydroxymethylcellulose and carboxymethylcellulose.

The content of other, preferably thermoplastic polymers, based on the total weight of compounds of the formula (1), is preferably 10 percent by weight to 2500 percent by weight, in particular 20 percent by weight, to 400 percent by weight.

The preparation of the conductive polymer in a matrix of another, preferably thermoplastic polymer, is described by European Patent Application No. 357,059, which corresponds to U.S. patent application Ser. No. 357,059, now abandoned filed Aug. 23, 1989.

Novel Conductive Polymers

Polymers which contain units of the formula (7):

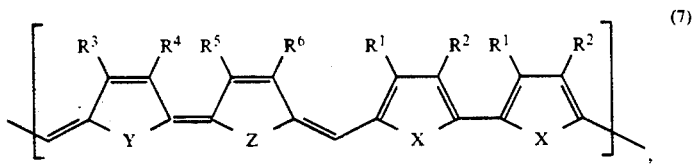

(7)

wherein $R^1$, $R^2$, $R^3$, $R^4$, $R^5$, $R^6$, X, Y and Z have the meanings given under formula (1), with the proviso that at least one of the rings according to formula (7) bonded by a group of the formula =CH— differs from the others by at least one of the radicals $R^1$, $R^2$, $R^3$, $R^4$, $R^5$, $R^6$, X, Y and Z, can also be prepared, inter alia, by polycondensation of compounds of the formula (1).

These are preferably polymers of the above-mentioned formula (7) to which X=Y=Z does not apply.

Polymers which contain units of the formula (7) are novel. Such polymers can be prepared by polycondensation of compounds of the formula (3), with the proviso that X=Y=Z does not apply.

The novel polymers according to the invention preferably contain at least 10 percent, particularly preferably at least 30 percent, in particular, at least 50 percent, especially at least 80 percent, in each case, based on the total weight of the polymer, of units of the formula (7).

The novel polymers according to the invention and compositions containing these polymers can additionally contain doping agents.

The polymers according to the invention can also be present, in finely divided form, in another, preferably thermoplastic polymer.

With regard to the doping agents and other polymers, preparation processes for the novel polymers and the like, the information set forth in the preceding section entitled, "Preparation of Polymers" applies accordingly.

BRIEF DESCRIPTION OF THE DRAWINGS

Other objects and features of the present invention will become apparent from the following detailed description considered in connection with the accompanying drawing and examples, which disclose one embodiment of the present invention. It should be understood, however, that these drawings and examples are designed for the purpose of illustration only and not as a definition of the limits of the invention.

In the drawing, wherein similar reference characters denote similar elements throughout the several views:

FIG. 2 shows the pronounced non-linear properties of coatings on quartz using the condensation product of the compound, which can be prepared according to Example 1.

DETAILED DESCRIPTION OF THE PREFERRED EMBODIMENT

Figure 1:
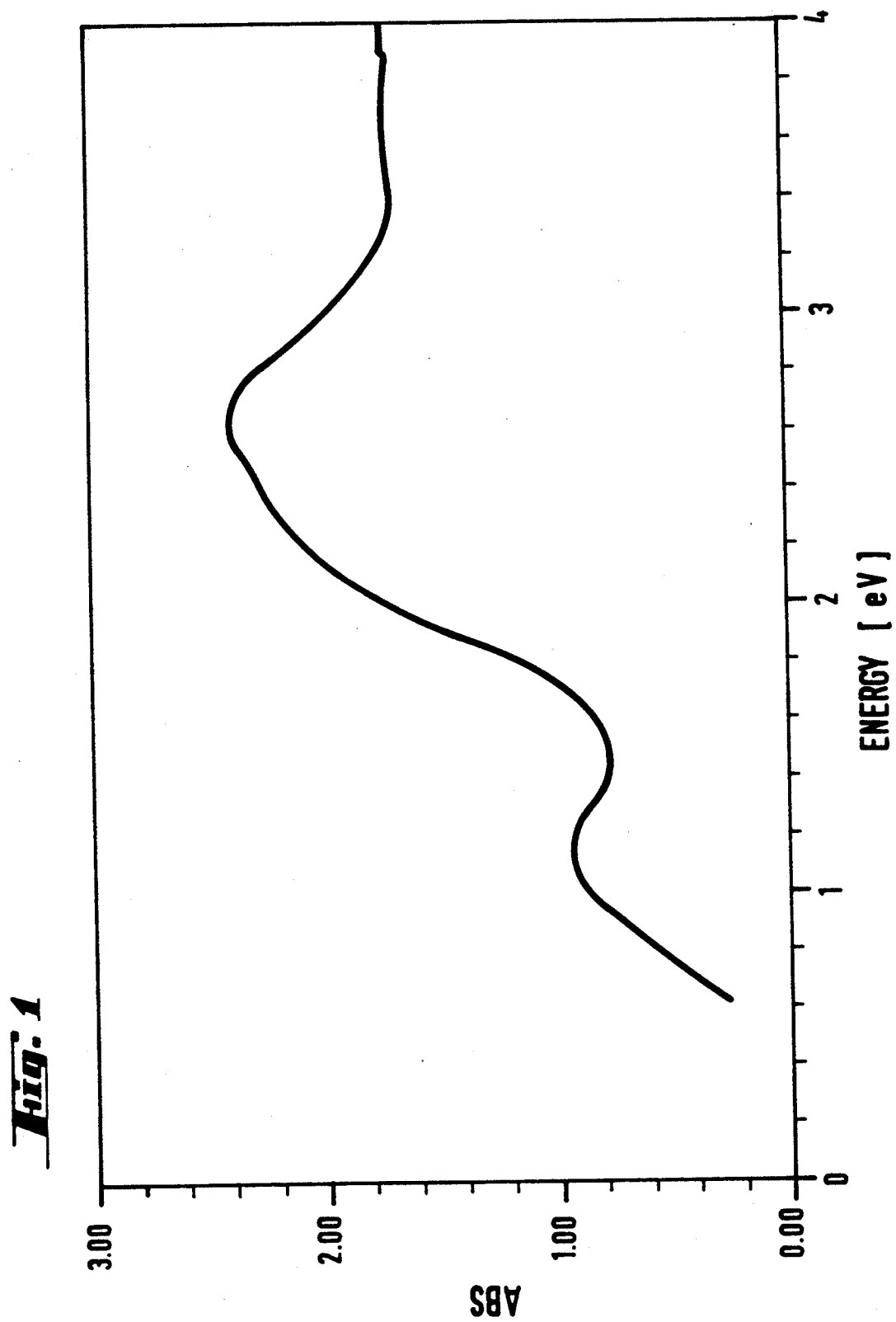
FIG. 1 shows a UV/VIS/IR spectrum of the condensation product prepared according to Example 12.

The polarization according to formula (1) of the rings containing the radicals X, Y and Z has an effect on the optical and electrical properties. If the highest possible electrical conductivities are required, compounds for which X=Y=Z will be employed. For use in the optical field, it may be desirable for the absorption to be shifted into certain wavelength ranges, which is possible, by suitable choice of X, Y and Z. For use for optical purposes, it may also be desirable for electron-donating groups, for example, amino, alkylamino or dialkyl-amino, or electron-withdrawing groups, for example, nitro or nitrile groups, to be introduced as at least one of the radicals $R^1$, $R^2$, $R^3$, $R^4$, $R^5$ and $R^6$ in formula (1).

The compounds according to the invention are outstandingly suitable for the preparation of thin layers which can be polycondensed by suitable condensing agents and converted into layers with particular electrical and optical properties. By use of the known mask technique, it is thus also possible to produce structures such as strip conductors or small structures on carriers, which are used as integrated sensors, transistors, photocells or other optical and electrooptical switches. The polymers prepared by the process according to the invention and the layers produced therefrom have diverse optical, photoelectrical and electrical properties. They have, in some cases, good electrical conductivities, are photoconductors and depending on the structure, have a band gap down to below one eV, that is to say, the photosensitivity extends into the infrared spectral region. FIG. 1 shows a UV/VIS/IR spectrum of the condensation produced prepared according to Example 12.

Polymers which contain units of the formula (13) have non-linear optical properties. Coatings on quartz using the condensation product of the compound which can be prepared according to Example 1 show pronounced non-linear properties (FIG. 2). The values measured for the non-linear susceptibility of the 3rd order lie in the order of size of $10^{-10}$ esu. The relaxation time observed in the picosecond range demonstrates the participation of resonant processes in the non-linear properties. That is to say, by suitable choice of the excitation wavelength, still far higher values of the non-linear susceptibility are to be expected. The relaxation components of 6 and 60 ps were measured for the relaxation properties of the non-linear refractive index by degenerate four-wave mixing (DFWM).

EXAMPLES

Unless otherwise stated, in each case, in the following examples: (a) all the amounts stated relate to the weight; (b) all the pressures are 0.10 MPa (absolute); and (c) all the temperatures are 20° C.

The following compounds of the formula (3) were prepared in the examples:

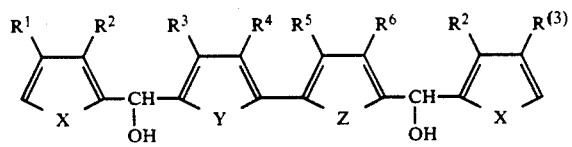

wherein
$R^3$, $R^4$, $R^5$ and $R^6$, in each case, denote hydrogen atoms, and Y and Z are, in each case, identical radicals, and wherein $R^1$, $R^2$, X, Y and Z have the meanings listed in the following Table 1:

TABLE 1

| Compound | Example No. | X | Y = Z | R¹ | R² |
|---|---|---|---|---|---|
| A | 1 | S | S | H | H |
| B | 2 | N—CH₃ | S | H | H |
| C | 3 | O | S | H | H |
| D | 8 | S | S | H | CH₃ |
| E | 4 | S | S | CH₃ | H |
| F | 5 | S | N—CH₃ | H | H |
| G | 6 | N—CH₃ | N—CH₃ | H | H |
| H | 7 | O | N—CH₃ | H | H |
| J | 11 | S | CH=CH | H | H |

Preparation of Compounds of the Formula (1)

Example 1

(Compound A)

13.8 ml of a 2.15 molar solution of butyllithium were added dropwise to 2.75 g (32.7 mmol.) of anhydrous thiophene in 25 ml of absolute diethyl ether at 0° C., under an argon atmosphere. After the end of the dropwise addition, the cooling was removed, and the mixture was boiled under reflux for 20 minutes. 3 g of 2,2'-bithienyl-5,5'-dialdehyde in a suspension, with 100 ml of anhydrous tetrahydrofuran were then added dropwise at 0° C. After the solution had been stirred at 0° C. for 4.5 hours, it was stored at 4° C. in a refrigerator for 17 hours. After addition of 6.5 ml of ammonium chloride solution saturated at room temperature and subsequent addition of dry ice for neutralization, the aqueous phase and the solids were separated off. After evaporation of the solvent and final drying under $10^{-3}$ mbar, 10.9 g=95% of theory of crude IIIa were obtained. NMR spectrum in acetone $D_6$: 7.40 ppm d, 2 H; 7.05 ppm d, 4 H; 6.97 ppm m, 2 H; 6.91 ppm d, 1 H; 6.30 ppm d, 1 H; 5.54 ppm d, 1 H.

Example 2

(Compound B)

16.2 ml (27.0 mmol) of a 1.59M n-butyllithium solution were added to a solution of 3.65 g (45 mmol) of N-methylpyrrole and 2.78 g (23.9 mmol) of tetramethylethylenediamine (TMEDA) in 15 ml of tetrahydrofuran and 15 ml of ether at room temperature. The mixture was then boiled under reflux for 1.5 hours until the evolution of gas (butane) had ended. The mixture was cooled at 0° C., and a suspension of 3.0 g (13.5 mmol) of 2,2'-bithineyl-5,5'-dialdehyde in 50 ml of tetrahydrofuran was added in the course of 30 minutes. The mixture was then stirred at room temperature for 17 hours. The mixture was stirred into 60 ml of a saturated ammonium chloride solution, while cooling with ice. The solution was extracted twice by shaking with 100 ml of ether. The combined ether extracts were dried over sodium sulfate. After the solvent had been evaporated off under a water pump vacuum, 5.8 g of a solid which was colored black-brown and was foamed in vacuo were obtained.

Example 3

(Compound C)

16.2 ml (27 mmol) of a 1.59M n-butyllithium solution were slowly added dropwise to a solution of 3.26 ml (45 mmol) of furan and 3.41 ml (27 mmol) of TMEDA in 30 ml of ether at 0° C., such that the temperature did not rise above 5° C. When the addition had ended, the mixture was heated and boiled under reflux for 2 hours. The pale beige precipitate which had separated out was dissolved by addition of 80 ml of tetrahydrofuran, and the mixture was cooled to $-14°$ C. 3.0 g (13.5 mmol) of 2,2'-bithienyl-5,5'-dialdehyde was added in portions at this temperature. The mixture was warmed slowly to 15° C., stirred at this temperature for 3.5 hours and then stirred into 200 ml of an ether/dry ice mixture. After thawing to room temperature, 200 ml of water were added. The ether phase was separated off, and the aqueous phase was brought to pH 3.5 with glacial acetic acid. The aqueous phase was then extracted 3 times by shaking with 100 ml of ether, and the combined ether extracts were neutralized with saturated sodium carbonate solution and rinsed with 2 portions of 50 ml of water. The ether fraction was dried over sodium sulfate. After the solvent had been stripped off, 3.6 g=74% of theory of a brown, highly viscous oil were obtained. H-NMR spectrum in chloroform $D_1$: 7.4 ppm d, 2H; 6.97 ppm d, 2H; 6.86 ppm d, 2H; 6.33 ppm m, 4H; 6.33 ppm s, 2H; 3.08 ppm s(b), 2H.

Example 4

(Compound E)

2.14 g (21.8 mmol) of 3-methylthiophene, 2 g of 2,2'-bithienyl-5,5'-dialdehyde and 10.25 ml of butyllithium solution (1.93 mol/l) were reacted analogously to Example 1. After the same work-up as in Example 1, 3.7 g=98% of theory of a partly crystalline, partly vitreous mass are obtained. The H-NMR spectrum shows that the 3-methylthiophene has not reacted unambiguously with the aldehyde group only at the 5-position, but that 17 percent of the thiophene units have reacted with the aldehyde function in the 2-position to give the compound D. According to the NMR spectrum, however, the main product corresponds to the desired product E. $^1$H-NMR spectrum in acetone $D_6$: 7.05 ppm d, 2H; 6.93 ppm m, 4H; 6.63 ppm s, 2H; 6.23 ppm s, 2H; 5.48 ppm s, 2H; 2.20 ppm s, 6H.

Example 5

(Compound F)

A solution of 5.0 g (31.2 mmol) of bis-N-methylpyrrole and 9.4 ml (62.4 mmol) of tetramethylethylenediamine (TMEDA) in 70 ml of hexane was cooled to 0° C. 45.8 ml (68.6 mmol) of a 1.5 molar n-butyllithium solution in hexane were slowly added to this mixture, such that the temperature did not rise above 3° C. When the addition had ended, the mixture was boiled under reflux for 30 minutes. The solution of the bislithiated bis-N-methylpyrrole was slowly added dropwise to a solution, cooled to 0° C., of 5.8 ml (62.4 mmol) of thiophene-2-carbaldehyde in 50 ml of ether, such that the temperature did not rise above 7° C. When the addition had ended, the mixture was heated to room temperature and stirred at this temperature for 3 hours. The mixture was poured into 150 ml of saturated ammonium chloride solution, while cooling with ice. The mixture was extracted 3 times by shaking with 100 ml of ether each time, and the combined ether fractions were washed twice with 50 ml of water each time. After drying over sodium sulfate, the solvent was stripped off under a water pump vacuum, and 7.5 g=62.5% of theory of a pale yellow orange solid were obtained, the solid becoming resinous after storage at 4° C. for about 2 weeks. H-NMR spectrum in chloroform $D_1$: 7.28 ppm d, 2H; 6.93 ppm m, 4H; 6.08 ppm m, 6H; 3.37 ppm s, 6H.

Example 6

(Compound G)

Dilithiated bis-N-methylpyrrole was prepared analogously to Example 5. 7.4 g (45.6 mmol) of bis-N-methylpyrrole, 11.6 ml (91.1 mmol) of TMEDA and 62.9 ml (100.2 mmol) of 1.59M n-butyllithium solution were used for this. After cooling to room temperature, the mixture was slowly added to a solution of 9.8 ml (91.1 mmol) of N-methylpyrrole-2-carbaldehyde in 70 ml of diethyl ether at 0° C., such that the temperature did not rise above 4° C. When the addition had ended, the mixture was warmed to room temperature, stirred for 3 hours and then cooled to 0° C., and 100 ml of a saturated ammonium chloride solution were added dropwise. After addition of 150 ml of ether, the aqueous phase was separated off and extracted twice more with 50 ml of ether each time. The combined ether extracts were washed with 2 portions of 50 ml of distilled water and dried over sodium sulfate. After removal of the solvent in vacuo, 13.9 g=80.5% of theory of a green-colored solid were obtained. For purification, 2 g of this product were dissolved in 100 ml of triethylamine, the undissolved material was filtered off, and 200 ml of hexane were slowly added at room temperature. The white precipitate which had separated out was filtered off and dried under $10^{-3}$ mbar, at room temperature, for 5 hours. H-NMR in chloroform $D_1$: 6.54, 6.06 ppm m, 12H; 3.62 ppm s, 2H; 3.34, 3.18 ppm m(b), 12H. Further purification of the product by chromatograpy was not possible because of the sensitivity to acids.

Example 7

(Compound H)

Analogously to Example 6, 5.0 g (30.8 mmol) of dilithiated bis-N-methylpyrrole were reacted with 5.0 g (62.4 mmol) of furfural in 50 ml of ether at 0° C., and the mixture was worked up. Yield: 9.8 g=90.3% of theory of an orange-red solid which was foamed in vacuo. H-NMR spectrum in chloroform $D_1$: 7.43 ppm d, 2H; 6.34 ppm m, 4H; 6.08 ppm, m, 4H; 5.86 ppm s, 2H; 3.45 ppm s, 2H; 3.42 ppm s, 6H.

Example 8

(Compound D)

6.30 g of dithienyl (37.9 mmol) in 25 ml of absolute ether were reacted with 35.3 ml of butyllithium (75.8 mmol) in hexane (2.15 mol/l) at 0° C. The mixture was then warmed to room temperature, 8.8 g (75.8 mmol) of tetramethylethylenediamine were added, and the mixture was heated under reflux for one hour. After cooling to 0° C., 9.6 g (75.8 ml) of 3- methyl-2-thienylaldehyde (manufacturer Janssen, the product contains about 8% of 4-methyl-2-thienylaldehyde) were added in 25 ml of absolute ether. The reaction mixture was stirred at room temperature for a further 17 hours and then hydrolyzed with 7 ml of aqueous NH$_4$Cl solution, saturated in the cold, and 15 ml of water. The mixture was decanted from the greasy residue which was deposited and, after removal of the aqueous layer, the ether layer was extracted twice, with 10 ml of water each time, and then evaporated in vacuo. The residue was then dissolved in 200 ml of isopropanol, together with the residue isolated previously by decanting, and the solution was filtered. After the filtrate had been left to stand overnight, 5.32 g=37% of theory of pale-yellow needles crystallized out. Melting point 182° C. H-NMR in acetone $D_6$: 7.02 ppm d, 2H; 6.79 ppm d 2H; 6.64 ppm d 2H; 6.59 ppm d 2H; 6.11 ppm s 1H; 5.27 ppm s 2H; 2.2 ppm s 6H. 9.1 g of a viscous resin which, according to NMR analyses, consisted of an isomer mixture due to the 4-methyl isomer of the aldehyde contained in the starting substance, were isolated from the evaporated isopropanol mother liquor.

Polycondensation of Compounds of the Formula (1)

Example 9

1.48 g of the compound A, which can be prepared according to Example 1, were dissolved in 25 ml of 1,2-dichloroethane. 72.4 mg of p-toluenesulfonic acid monohydrate in 30 ml of hot 1,2-dichloroethane were added to this solution. After the mixture had been boiled under reflux for 4½ hours, it was cooled to room temperature, and 480 mg of iodine in 12 ml of 1,2-dichloroethane were added dropwise at 24° C. After the mixture had been left to stand overnight, the precipitate which had separated out was filtered, washed five times with 5 ml of 1,2-dichloroethane each time, and dried under $10^{-3}$ mbar. Yield: 1.87 g; conductivity $5 \times 10^{-5}$ S/cm.

Coatings by Polycondensation of Compounds of the Formula (1) on Substrates

Example 10

150 mg of furfuryl alcohol and 147 mg of 2-furaldehyde were dissolved in 8.3 ml of a 1 percent strength solution of PVC in tetrahydrofuran (PVC: manufacturer: Wacker-Chemie GmbH; type designation Y61 M, reprecipitated from tetrahydrofuran with methanol for after-purification). Some of this solution was applied to a microscope slide until the slide was completely covered, using a pipette. The solvent was then allowed to evaporate in a stream of argon, and the microscope slide was subsequently placed in a Petri dish, into which 2 ml of POCl$_3$ had first been introduced, using two glass rods as spacers. After 18 hours, the microscope slide was removed and placed in concentrated hydrochloric acid for 5 minutes, during which the coating became detached as a film. After drying at room temperature, it had a thickness of 20 μ and a conductivity of $1 \times 10^{-2}$ S/cm.

Production of Polymer Films

Example 11

Analogously to Example 10, a solution of the diol, together with PVC (type as the Example in 10) was prepared to produce free-standing films in polymer matrices. The amounts of monomer in respect of PVC can be seen from Table 2. The solution was spread onto a glass surface with the aid of a film doctor blade (250 μm), and the solvent was evaporated off by leaving the glass surface in the air for 2 to 3 hours. Test specimens (6×2 cm$^2$) were cut out of the still swollen polymer film thus produced and were placed on a microscope slide. The pieces of film were fixed to the microscope slide, at both ends, using Teflon insulating tape. The samples were then placed on a spacer in a Petri dish with a ground-glass rim, which contained, in each case, 5 ml of phosphorus oxychloride or 37% strength aqueous hydrochloric acid solution.

After the reaction time shown in Table 2, the samples were removed from the vessel and dried at room temperature under 1 mbar for 2 hours and then under $10^{-4}$ mbar for 7 hours. If appropriate, after-treatment followed. In this, the samples were either placed in an iodine vapor atmosphere or placed in a drying cabinet for the times shown in Table 2, at the temperatures shown. In the case of iodine doping, the sample was also evacuated under 0.1 mbar for 2 hours.

panes were placed on a glass frame in a 1 l vessel with a plane-ground lid. The polycondensation of the compounds of the formula (3) was carried out by 4 different processes: (a) introduction of gaseous HCl via a glass tube which extends to the bottom of the vessel; (b) introduction of 2 ml of a liquid condensing agent on the

TABLE 2

Polycondensation in Other Polymers (Polymer Composites)

| Compound of Table 1 | PVC [mg] | Volume of the solution [ml] | Condensing agent | Reaction Time [min] | Temp. [°C.] | Conductivity [S/cm] | Layer thickness [μm] | |
|---|---|---|---|---|---|---|---|---|
| A | 215 | 700 | 10 | POCl$_3$ | 10 | 50 | $2.3 \times 10^{-4}$ | 30 | |
| A | 215 | 700 | 10 | POCl$_3$ | 20 | 50 | $8.3 \times 10^{-4}$ | 19 | |
| A | 215 | 700 | 10 | POCl$_3$ | 30 | 50 | $1.1 \times 10^{-3}$ | 15 | |
| A | 215 | 700 | 10 | POCl$_3$ | 10 | 50 | $1.1 \times 10^{-4}$ | 33 | 1 |
| F | 185 | 695 | 10 | HCl | 10 | 20 | $1.8 \times 10^{-10}$ | 16 | |
| F | 185 | 695 | 10 | HCl | 10 | 20 | $6.0 \times 10^{-10}$ | 20 | 2 |
| F | 185 | 695 | 10 | HCl | 10 | 20 | $1.5 \times 10^{-10}$ | 19 | 3 |
| F | 185 | 695 | 10 | POCl$_3$ | 10 | 20 | $7.4 \times 10^{-4}$ | 27 | |
| F | 185 | 695 | 10 | POCl$_3$ | 10 | 20 | $7.1 \times 10^{-4}$ | 25 | 2 |
| F | 185 | 695 | 10 | POCl$_3$ | 10 | 20 | $7.5 \times 10^{-4}$ | 21 | 3 |
| J | 210 | 700 | 10 | POCl$_3$ | 20 | 50 | $2.5 \times 10^{-3}$ | 36 | 4 |
| J | 210 | 700 | 10 | POCl$_3$ | 10 | 50 | $2.7 \times 10^{-4}$ | 17 | 4 |
| J | 210 | 700 | 10 | POCl$_3$ | 10 | 50 | $3.4 \times 10^{-4}$ | 21 | 5 |
| G | 210 | 700 | 10 | HCl | 10 | 20 | $6.8 \times 10^{-9}$ | 18 | |
| G | 210 | 700 | 10 | HCl | 10 | 20 | $1.6 \times 10^{-9}$ | 16 | 6 |
| G | 210 | 700 | 10 | HCl | 10 | 20 | $1.7 \times 10^{-9}$ | 23 | 2 |
| G | 210 | 700 | 10 | HCl | 10 | 20 | $7.4 \times 10^{-8}$ | 12 | 8 |
| G | 210 | 700 | 10 | POCl$_3$ | 10 | 20 | $3.6 \times 10^{-3}$ | 26 | |
| G | 210 | 700 | 10 | POCl$_3$ | 10 | 20 | $1.3 \times 10^{-2}$ | 20 | 7 |
| G | 210 | 700 | 10 | POCl$_3$ | 10 | 20 | $2.6 \times 10^{-3}$ | 36 | 2 |
| G | 210 | 700 | 10 | POCl$_3$ | 10 | 20 | $6.7 \times 10^{-3}$ | 26 | 8 |

After Treatment of the Samples:
1 3 hours iodine;
2 1 hours/70° C.;
3 1 hour/70° C. — 1 hour iodine
4 1 hour/67° C.;
5 1 hour/80° C.;
6 1 hour iodine;
7 1 hour iodine, 1 hour 60° C.;
8 1 hour/70° C., 1 hour iodine, 1 hour/60° C.

EXAMPLE 12

Coatings With Compounds of the Formula (3)

Compounds of the formula (3), according to Table 1, were dissolved in a concentration of 30 mg/ml in a 1 percent strength solution of PVC in tetrahydrofuran (type as Example 11) or a 1 percent strength solution of poly-N-vinyl-carbazole in tetrahydrofuran. Panes of glass of 7.6 cm (3") diameter were coated with this solution by the spin coating process (700–1000 revolutions per minute). The solvent was evaporated off by passing over a stream of argon, and several coated panes were placed on a glass frame in a 1 l vessel with a plane-ground lid. The polycondensation of the compounds of the formula (3) was carried out by 4 different processes: (a) introduction of gaseous HCl via a glass tube which extends to the bottom of the vessel; (b) introduction of 2 ml of a liquid condensing agent on the bottom of the reaction vessel and evacuation, at room temperature, until the condensing agent started to boil; (c) evacuation of the glass container to $10^{-3}$ mbar and introduction of a stream of the condensing agent vapor from a storage container containing liquid condensing agent, up to the saturation vapor pressure at room temperature; (d) evacuation of the glass container to $10^{-3}$ mbar and vaporization of 10 μl of a liquid condensing agent from a storage container of 5 ml capacity, which was cooled with liquid nitrogen during the evacuation.

The conditions and results of these coatings are shown in the following Table 3

TABLE 3

Production and Properties of Conductive Coatings According to Example 12

| Compound of Table 1 | X[a] | Condensing Agent | Time [h] | Thickness [μ] | Conductivity [S/cm] | $\epsilon^{b)}$ [cm$^{-1}$] |
|---|---|---|---|---|---|---|
| A | a | HCl | 120 | — | — | 6000 |
| A | b | BF$_3$ etherate | 24 | 0.35 | $3.70 \times 10^{-8}$ | — |
| A | b | CF$_3$COOH | 24 | 0.55 | $2.00 \times 10^{-6}$ | 10400 |
| A | c | CF$_3$COOH | 24 | 0.92 | $1.07 \times 10^{-4}$ | 10100 |
| A | c | CF$_3$COOH[c] | 24 | 0.96 | $1.40 \times 10^{-8}$ | 9370 |
| A | c | POCl$_3$ | 24 | 1.70 | $8.50 \times 10^{-4}$ | 4760 |
| A | d | CF$_3$COOH | 24 | 0.72 | $5.00 \times 10^{-9}$ | 9500 |
| G | a | HCl | 120 | — | — | 0 |
| G | b | BF$_3$ etherate | 24 | 0.35 | $4.50 \times 10^{-8}$ | — |
| E | c | POCl$_3$ | 24 | 1.17 | $6.00 \times 10^{-4}$ | 3960 |
| E | d | CF$_3$COOH | 24 | 0.50 | $9.00 \times 10^{-8}$ | 17000 |
| D | a | HCl | 120 | — | — | 3200 |
| D | b | BF$_3$ etherate | 24 | 0.35 | $2.80 \times 10^{-8}$ | — |
| D | b | CF$_3$COOH | 24 | 0.32 | $2.00 \times 10^{-8}$ | 11300 |
| D | c | CF$_3$COOH | 24 | 0.47 | $1.70 \times 10^{-8}$ | 10900 |
| D | c | CF$_3$COOH[c] | 24 | 0.62 | $1.00 \times 10^{-8}$ | 7740 |
| D | c | POCl$_3$ | 24 | 0.92 | $3.00 \times 10^{-5}$ | 3260 |

TABLE 3-continued

Production and Properties of Conductive Coatings According to Example 12

| Compound of Table 1 | X[a] | Condensing Agent | Time [h] | Thickness [μ] | Conductivity [S/cm] | ε[b] [cm$^{-1}$] |
|---|---|---|---|---|---|---|
| D | d | CF$_3$COOH | 24 | 0.40 | 1.30 × 10$^{-8}$ | 11000 |

[a]condensation method
[b]extinction at the maximum at about 1100 nm
[c]polyvinylcarbazole as the polymer matrix

Example 13

Coatings With Compounds of the Formula (3) On Polymer Films

Compounds of the formula (3), according to Table 1, were dissolved in chloroform in the concentrations shown in Table 4. The solutions were applied to polymer films (polyester: AMOTRANS R 40 copying film, Messerli AG, Switzerland; rigid PVC: Wacker-Chemie), with a wet film thickness of 250 μm, using a doctor blade. After a drying time of 30 minutes, test specimens (6×2 cm$^2$) were cut out and fixed with a Teflon insulating tape, with the coated side upwards.

Treatment of the samples was as described in Example 11. In the case of condensation with p-toluene-sulfonic acid solution, the test specimen was placed in a 10 percent strength aqueous p-toluenesulfonic acid solution.

The films coated with the diol, in most cases, discolored to dark blue or black immediately on contact with the condensing agent. The coating was mechanically stable and scratch resistant. Transparent, conductive coatings could be produced, depending on the concentration of the compound of the formula (3) in the starting solution.

TABLE 4

Production and Properties of conductive Coatings According to Example 13

| Compound | Concentration of the Solution [mg/ml] | Polymer Matrix | Condensing agent | Time [min] | Surface Resistance [Ohm] |
|---|---|---|---|---|---|
| G | 5 | Polyester | HCl | 10 | 4.5 × 10$^{11}$ |
| G | 5 | " | POCl$_3$ | 10 | 5.8 × 10$^8$ |
| G | 5 | " | p-TosH | 10 | 2.0 × 10$^{12}$ |
| G | 10 | " | HCl | 10 | 3.0 × 10$^{11}$ |
| G | 10 | " | p-TosH | 10 | 2.0 × 10$^{12}$ |
| G | 20 | " | HCl | 10 | 5.7 × 10$^7$ |
| G | 20 | " | POCl$_3$ | 10 | 4.1 × 10$^8$ |
| G | 20 | " | p-TosH | 10 | 9.7 × 10$^7$ |
| G | 5 | PVC, rigid | HCl | 10 | 5.3 × 10$^{11}$ |
| G | 5 | " | POCl$_3$ | 10 | 7.8 × 10$^{11}$ |
| G | 20 | " | HCl | 10 | 1.2 × 10$^9$ |
| G | 20 | " | POCl$_3$ | 10 | 2.9 × 10$^{11}$ |
| G | 20 | " | p-TosH | 10 | 3.6 × 10$^{11}$ |
| A | 20[a] | Polyester | HCl | 60 | 1.9 × 10$^8$ |
| A | 20[a] | " | POCl$_3$ | 10 | 3.2 × 10$^6$ |
| A | 20[a] | " | p-TosH | 10 | 2.0 × 10$^{12}$ |
| A | 20[b] | PVC, rigid | HCl | 60 | 1.0 × 10$^{12}$ |
| A | 20[b] | " | HCl | 300 | 5.0 × 10$^{11}$ |
| A | 20[b] | " | POCl$_3$ | 10 | 8.2 × 10$^6$ |
| A | 20[b] | " | p-TosH | 10 | 5.2 × 10$^{11}$ |
| F | 20 | Polyester | HCl | 10 | 4.0 × 10$^{11}$ |
| F | 20 | " | POCl$_3$ | 10 | 9.0 × 10$^9$ |
| F | 20 | " | p-TosH | 10 | 4.0 × 10$^{11}$ |

[a]Solvent: tetrahydrofuran
[b]Solvent: tetrahydrofuran/CHCl$_3$ = 1:4 parts by volume.

While only a single embodiment of the present invention has been shown and described, it is to be understood that many changes and modifications may be made thereunto, without departing from the spirit and scope of the invention as defined by the appended claims.

What is claimed is:

1. A compound of the formula (1)

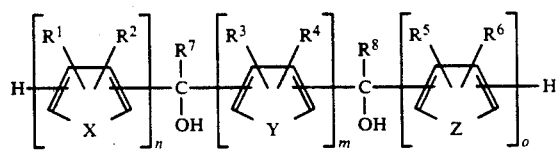

wherein
R$^1$, R$^2$, R$^3$,
R$^4$, R$^5$ and R$^6$ which may be identical or different radicals on the rings, denote hydrogen atoms, halogen atoms, straight-chain or branched C$_1$- to C$_6$-alkyl radicals, C$_1$- to C$_6$-alkylcarboxylic acid radicals or esters thereof with C$_1$- to C$_4$-alkanols, C$_1$- to C$_6$- alkylamino radicals or nitro or cyano groups, wherein at least two of the radicals R$^1$, R$^2$, R$^3$, R$^4$, R$^5$, and R$^6$ can be linked to one another in pairs and form a trimethylene or tetramethylene group;
X, Y and Z denote identical or different divalent radicals —O—, —S—, —N(R$^9$)— or —C(R$^{10}$)=C(R$^{11}$)—, with the proviso that at least one of the radicals X, Y and Z is not a radical of the formula —C(R$^{10}$)=C(R$^{11}$)—, and wherein
R$^9$ is a hydrogen atom, a branched or unbranched C$_1$- to C$_8$-alkyl radical or a phenyl radical;
R$^{10}$ and R$^{11}$ are, in each case, identical or different radicals which have one of the meanings of R$^1$;

R[7] and R[8] denote identical or different radicals selected from hydrogen atoms or $C_1$- to $C_6$-alkyl or phenyl radicals; and n, m and o denote identical or different integers with a value of from 1 to 10.

2. A compound of the formula (2)

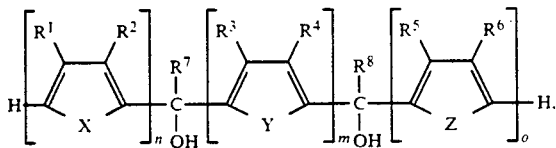

wherein R[1], R[2], R[3], R[4], R[5], R[6], R[7], R[8], X, Y, Z, m, n and o have the meanings given in claim 1.

3. A compound of the formula (3)

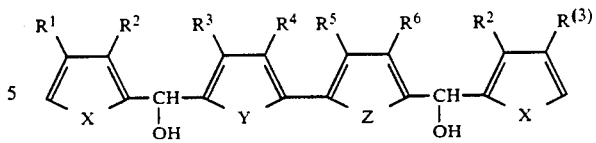

wherein X, Y, Z, R[1], R[2], R[3], R[4], R[5] and R[6] have the meaning given in claim 1.

4. A polymer which contains units of the formula

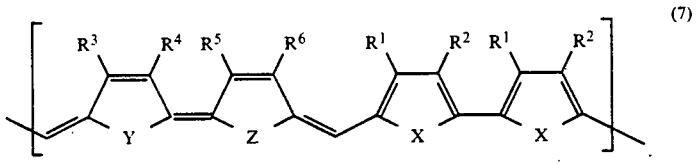

wherein R[1], R[2], R[3], R[4], R[5], R[6], X, Y and Z have the meanings given in claim 1, with the proviso that at least one of the rings according to formula (7) bonded by a group of the formula =CH— differs from the others by at least one of the radicals R[1], R[2], R[3], R[4], R[5], R[6], X, Y and Z.

5. A polymer as claimed in claim 4, additionally containing a doping agent.

6. A composition comprising the polymer of claim 4, with a doping agent additionally being present within the polymer.

7. A composition comprising the polymer of claim 4, in finely divided form within another polymer selected from the group consisting of an organic synthetic polymer, a naturally occurring polymer and a semisynthetic high molecular weight compound.

8. A composition as claimed in claim 7, wherein the organic synthetic polymer is a thermoplastic polymer.

* * * * *